(12) United States Patent
DeFeo

(10) Patent No.: US 6,493,578 B1
(45) Date of Patent: Dec. 10, 2002

(54) PORTABLE TENSION AND STRESS DETECTOR AND METHOD

(76) Inventor: Michael DeFeo, Rye, NY (US)

( * ) Notice: Subject to any disclaimer, the term of this patent is extended or adjusted under 35 U.S.C. 154(b) by 0 days.

(21) Appl. No.: 09/407,903

(22) Filed: Sep. 29, 1999

(65) Prior Publication Data (65)

(51) Int. Cl.[7] .................................................. A61B 5/05
(52) U.S. Cl. ....................................................... 600/546
(58) Field of Search .............................. 600/27, 28, 29, 600/544, 545, 546, 547

(56) References Cited

U.S. PATENT DOCUMENTS

| 4,031,883 A | * | 6/1977 | Fehmi et al. | |
| 4,170,225 A | * | 10/1979 | Criglar et al. | |
| 4,896,675 A | | 1/1990 | Oshuga | |
| 5,304,112 A | | 4/1994 | Mrklas et al. | |
| 5,343,871 A | | 9/1994 | Bittman et al. | |
| 5,568,814 A | | 10/1996 | Gallant et al. | |
| 5,694,939 A | | 12/1997 | Cowings | |
| 5,730,140 A | | 3/1998 | Fitch | |
| 6,006,129 A | * | 12/1999 | Watson | 600/546 |
| 6,026,321 A | * | 2/2000 | Miyata et al. | 600/546 |

* cited by examiner

*Primary Examiner*—Scott M. Getzow

(57) ABSTRACT

A small portable instrument monitors residual muscle tension as indicated by electrical activity from electrodes monitoring the muscles. A bio feedback signal is generated whenever tension exceeds a preset threshold and slows or stops as the tension is reduced towards the threshold. The bio feedback signal enables the user to learn how to voluntarily reduce excess muscle tension and lessen harmful health effects caused by stress. The instrument is battery powered, miniaturized and is designed to fit into an ambulatory setting.

32 Claims, 8 Drawing Sheets

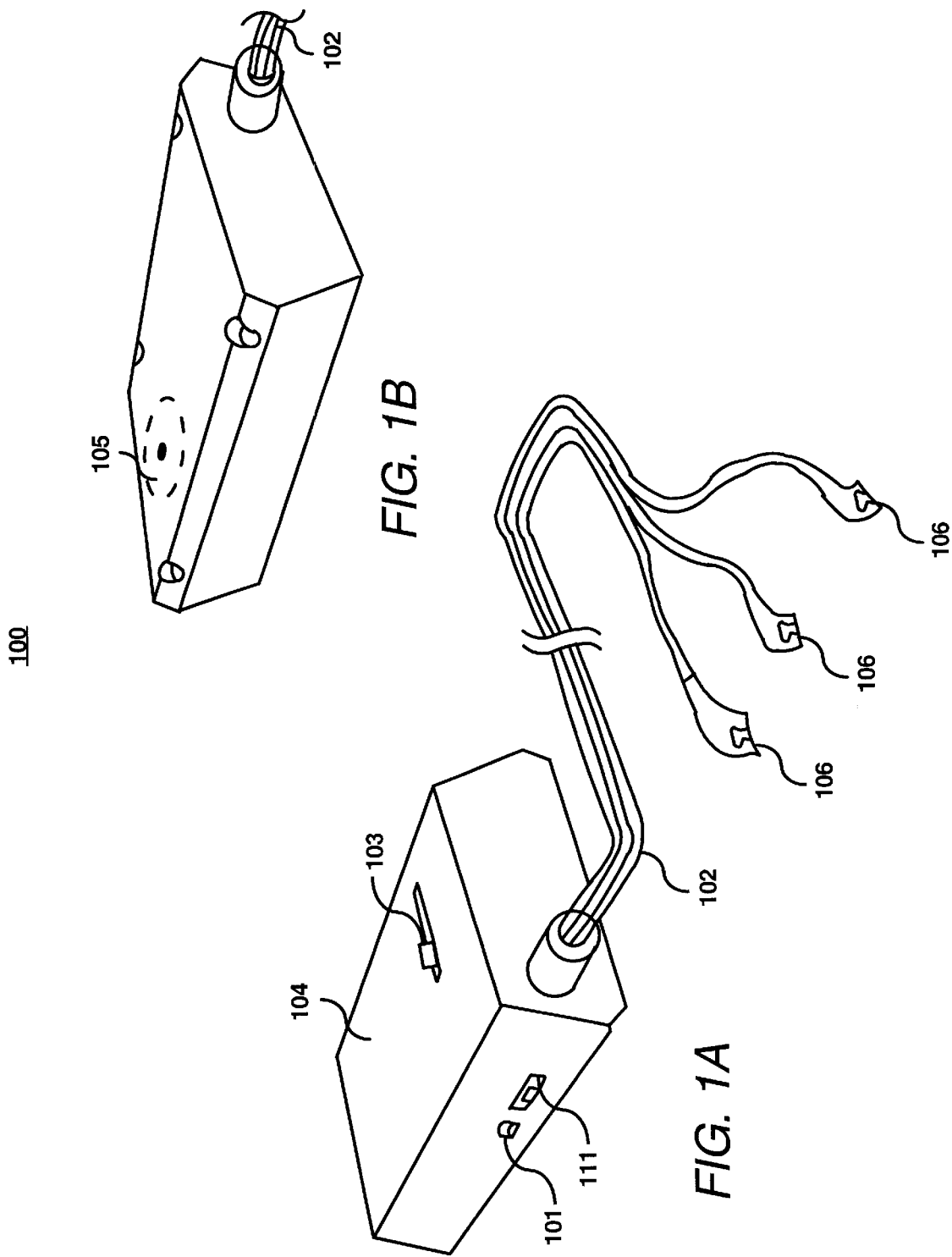

PORTABLE TENSION AND STRESS DETECTOR AND METHOD

FIELD OF THE INVENTION

The invention relates to a portable apparatus and a method for detecting and reducing tension and stress in a human subject using bio feedback.

BACKGROUND

Stress is an everyday fact of life for millions of people. Stressful situations are often found in the workplace and at home. This stress can lead to long-term physical and psychological problems. Research has shown that stress can be reduced through the alteration of brain wave patterns that the brain uses in order to function. Stimuli, such as sound and light, can affect and actually alter the flow of these brain wave patterns.

Bio feedback systems are known in the art for use in detecting levels of stress in subjects and providing the appropriate stimuli to affect and alter the flow of brain wave patterns. Bio feedback systems monitor and process bioelectrical signals generated in specific topological regions of a human subject's nervous system and produce a sensory stimulus when the system detects the presence or absence of certain characteristics in the signal. These characteristics may be correlated with a desired condition of the human subject's nervous system. The sensory stimulus provided by the bio feedback system, typically an audio or visual stimulus, or a combination of the two, is fed back to the human subject who associates the presence of the stimulus with the goal of achieving the desired condition of the nervous system. By responding to the stimulus, the human subject can be trained to control the wave form patterns of the monitored bioelectrical signals and thereby control the nervous system. Such a bio feedback system is disclosed in U.S. Pat. No. 3,727,616 to Ross.

Because bio feedback devices operate on the basis of internal stimuli, that is stimuli produced in response to bioelectrical signals generated by the human subject, the success of the bio feedback device depends upon a human subject attempting to consciously control a state of stress. Many people cannot affect such control over their involuntary nervous systems. In addition, bio feedback systems are usually expensive, require complex equipment, and require an expert to operate.

Prior art devices have attempted to overcome these limitations by producing a state of mental harmonization or relaxation in a human subject without detecting the state of stress, that is, through the use of a program of external stimuli. However, such systems do not provide a stress detection system and, therefore, the stimuli cannot be tailored to a human subject's changing state of stress and individual needs.

SUMMARY OF THE INVENTION

Tension and stress in human subjects may result in involuntary muscle movement. This muscle activity in the human body is initiated by electrical nerve impulses from the brain. These impulses may be measured at the surface of the skin as a voltage. The magnitude of the voltage signal is very small, on the order of micro volts. The magnitude of the electrical activity varies proportionately with the force of the muscle movement.

A small portable instrument is used to monitor residual muscle tension, as indicated by electrical activity from spurious motor neuron firings. The instrument is connected to one or more electrodes that receive electrical impulses created by activated nerves in the human subject's muscle groups. A bio feedback signal is generated whenever tension exceeds a pre-set threshold and slows or stops as tension is reduced towards the threshold. This enables the user to learn how to voluntarily reduce excess muscle tension and lesson the harmful health effects caused by stress. The instrument is battery powered and is miniaturized to fit comfortably on a human subject, such as in a shirt pocket. Alternatively, the instrument may be attached to the clothing of the human subject by velcro or by a clip-on device, or may be attached to the body of the human subject using a band with a velcro fastener, for example.

In an embodiment, three electrodes are attached to the skin of the human subject, along a chosen muscle group. A sensitive instrument amplifier detects differential voltage, while rejecting common mode signals. The desired signals are isolated through a band pass filter, of approximately 100 Hz, for example. The signals are then amplified. Signals that exceed a set point are integrated and produce a feedback signal through a small speaker, at a rate proportional to the amount of muscle tension.

The electrodes may be attached to the human subject on a desired muscle group, such as the trapezius muscles (shoulder and back), for example.

The instrument is ideal for a person sitting at a desk, using a computer keyboard, or any other position or situation where a person has a tendency to build up tension and stress in the neck, shoulders and back muscles. Such stress, if not reduced, may cause disturbing irritability, headaches, shoulder pain, back pain, carpal tunnel syndrome, tingling and numbness in fingers, hands and arms, or any other pain associated with stress buildup.

The apparatus and method may be used by the human subject to learn when tension and stress will occur. By repeatedly using the apparatus, the human subject will learn what activities or conditions are likely to cause high levels of tension and stress. The human subject can then modify or avoid the activities or conditions so as to prevent the buildup of harmful stress.

BRIEF DESCRIPTION OF THE DRAWINGS

The invention will be described with reference to the following drawings, in which like numerals refer to like items and wherein:

FIG. 1a is a top perspective view of a portable apparatus for detecting and measuring tension and stress in a human subject and displaying an indication thereof;

FIG. 1b is a bottom perspective view of the apparatus of FIG. 1a;

FIG. 3 is a block diagram of the apparatus of FIG. 1a;

FIG. 4 is a schematic diagram of a control and display circuit of the apparatus of FIG. 1a; and FIG. 5 is a schematic diagram of a power supply of the apparatus of FIG. 1a.

DETAILED DESCRIPTION

Figure 2A:
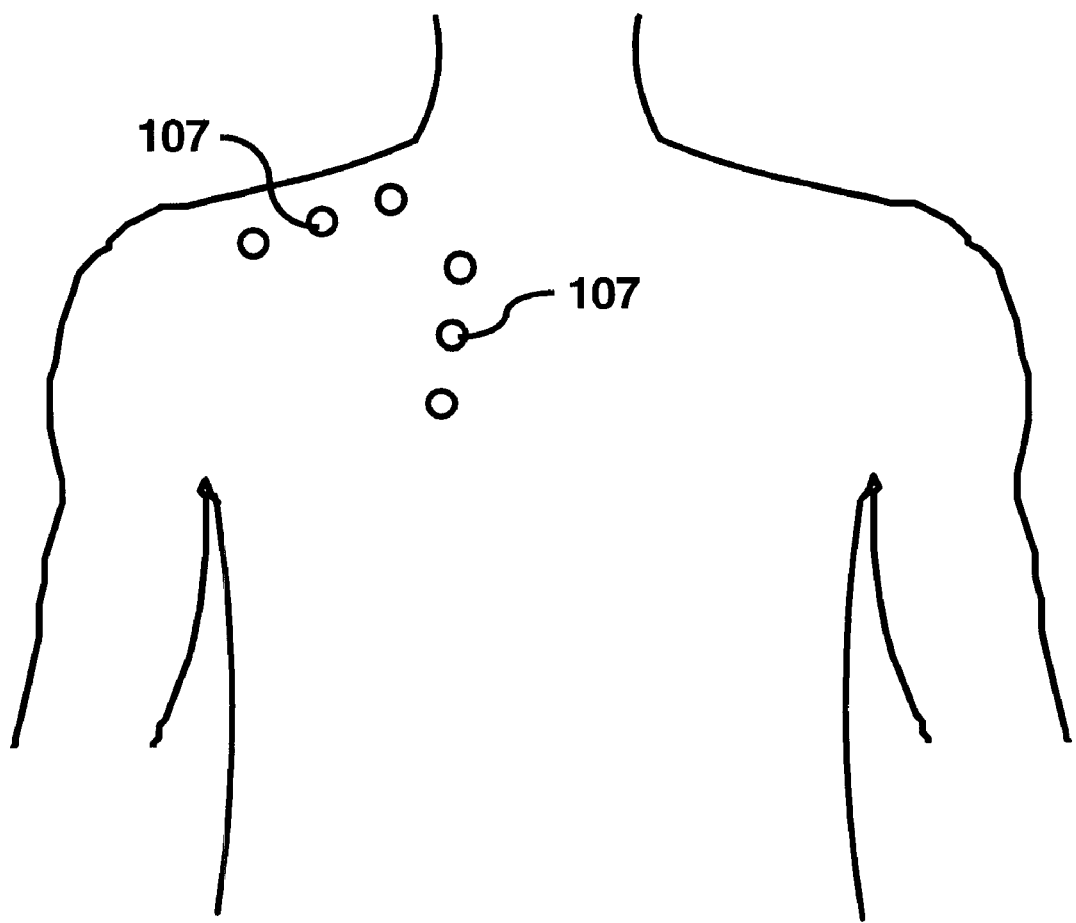
FIGS. 2a–2d illustrate example measurement points on the human subject.

The invention is a portable apparatus and a method for detecting tension and stress in a human subject and for displaying an indication of such stress. The apparatus and method offer considerable advantage over prior art systems.

In particular, the apparatus does not require a skilled operator to install or monitor and provides an output that is readily understood by the human subject, even when the human subject has no training in interpreting bio feedback responses. Moreover, the apparatus is adjustable so that the apparatus can be used by different individuals without a time consuming and costly calibration. The apparatus is portable, making it ideal for ambulatory subjects. Thus, the apparatus is readily usable in a variety of work environments. Costly overhead, clinics and other complications associated with traditional bio feedback systems are eliminated by the invention. The invention allows a human subject to readily and easily self-monitor for the onset of excessive tension and stress. The invention also allows the human subject to learn which situations are likely to cause tension and stress, and to therefore avoid such situations.

Stress may be detected by a number of different mechanisms. For example, higher breathing rates and heart rates are often associated with high levels of stress. Similarly, galvanometric skin resistance and brain wave activity can also be used to measure stress. In addition, stress in human subjects may cause muscles, such as the muscles of the neck, upper back and shoulders to contract. This contraction generates small but measurable voltages on the skin surface. These voltages, in the microvolt range, can be detected by using sensitive electrode sensors attached to the skin along the muscle of interest.

FIG. 1a shows a top perspective view of a portable apparatus 100 for detecting and indicating stress in a human subject. The apparatus 100 includes a casing 104 enclosing the electronics of the apparatus 100. The casing 104 is small and lightweight, and may be sized to fit into any shirt pocket or may clip on, for example. The casing 104 may have a length of four inches, a width of 2.5 inches and a thickness of one inch, for example, and can be made even smaller. The casing 104 may be formed from any suitable plastic material or from a lightweight metal, or a combination of the two. The electronics of the apparatus 100 will be described in detail later. The apparatus 100 includes an on/off switch 101 by which electrical power is connected to the electronics. Signals from the human subject are provided to the apparatus 100 through wiring harness 102. Wires in the wiring harness 102 terminate in attachments 106 that may be used to connect to electrodes (not shown). The electrodes are mounted directly on the human subject's chosen muscle group by way of adhesion, for example. The attachments 106 may be snap connections that are easily attached to and removed from the electrodes.

Also shown in FIG. 1a is a volume control switch 111 that is used to control an output volume of the apparatus 100 and a threshold switch 103 that is used to set a threshold value to indicate an onset of stress. The switch 103 may be a slider switch, for example. Using the switch 103, the human subject can select an onset level, which, when exceeded, will lead the apparatus 100 to produce an audible output signal. The volume control switch 111 can be used to vary the intensity of the output audible signal. In use, the apparatus 100 can be placed in a shirt pocket, may be attached using a velcro fastener, or may clip on, for example. The wiring harness 102 can then be led to electrode attachment points on the human subject's muscle group.

FIG. 1b shows a bottom perspective view of the apparatus 100. As shown in FIG. 1b, the apparatus 100 includes a speaker face 105 through which the audible signal generated by the apparatus 100 is provided for display to the human subject.

While FIG. 1a shows the apparatus 100 including a wiring harness 102, the apparatus 100 could also incorporate a radio frequency receiver that receives a radio frequency signal from wireless electrodes attached to the human subject. In this alternative, the wiring harness 102 is not required. Such an arrangement would increase the portability of the apparatus 100 and may make the apparatus 100 even more acceptable in a work environment. FIG. 2a shows possible contact points 107 for attaching the electrodes associated with the apparatus 100 to the human subject. As shown in FIG. 2a, the three contact points 107 are displayed along the shoulder or the upper back muscles (e.g., the trapezius or the latisimus dorsi) of the human subject. As shown in FIG. 2a, and as will be discussed below with respect to the electronics of the apparatus 100, three electrode contact points may be selected. However, the apparatus 100 is not limited to the use of three contact points. Any number of electrode contact points may be implemented in the apparatus 100.

Figure 2B:
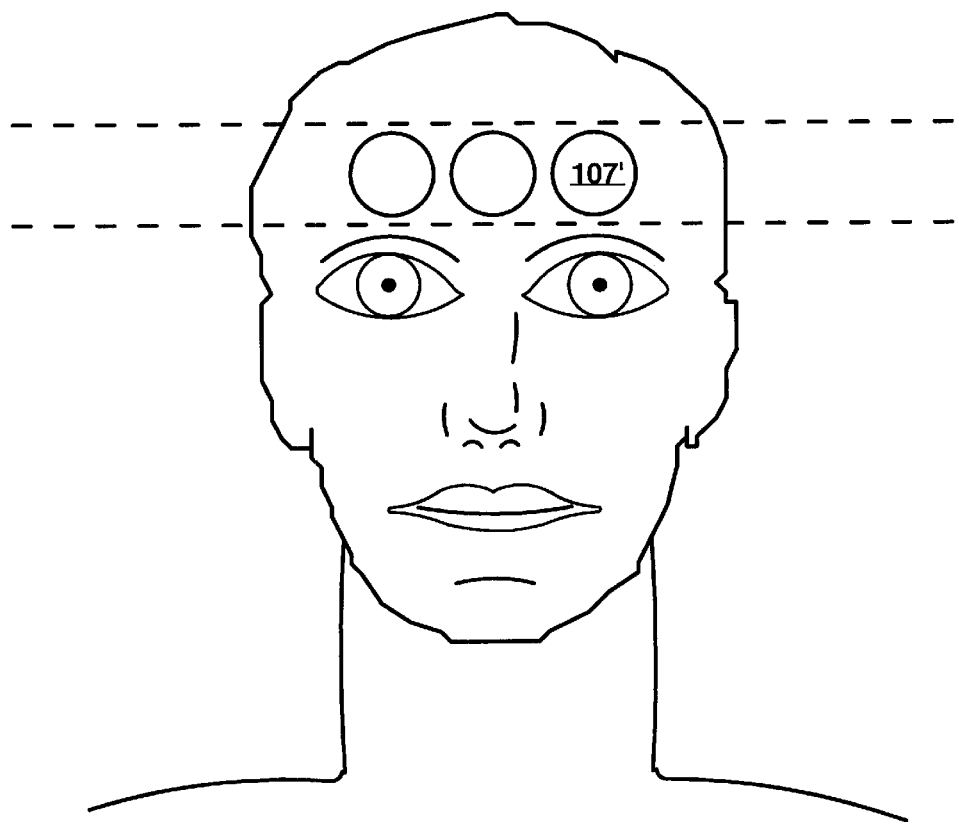
Figure 2C:
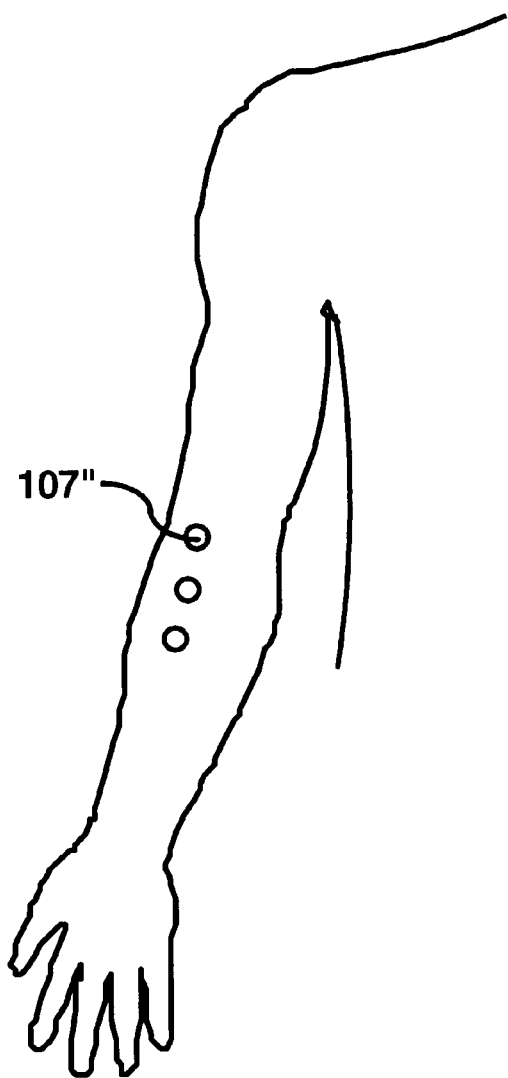
Figure 2D:
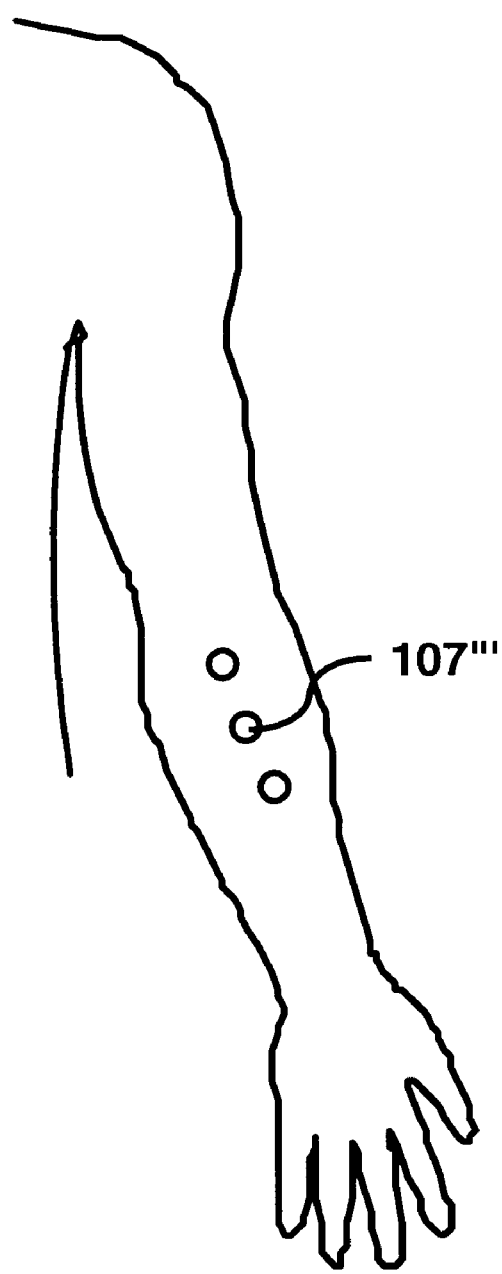

FIGS. 2b–2d show alternate contact points for the electrodes. FIG. 2b shows contact points 107' on the forehead. FIG. 2c shows contact points 107" on the forearm flexor. FIG. 2d shows contact points 107'" on the forearm extender.

Although FIGS. 2a–2d show three separate contact points, indicating separate attachment of three electrodes to the human subject, one or more electrodes may be incorporated into a strap or band that is then attached to the human subject. The band 109 is designed to place the electrodes 108 over a surface of the chosen muscle group. For example, the electrodes 108 could be incorporated into a band that fits around the human subject's chest. When worn, the band may then place the electrodes 108 over the latisimus dorsi muscles, for example. The electrodes 108 may be of a conventional design and may be coupled to the apparatus 100 using the wiring harness 102. Alternatively, the electrodes 108 may incorporate radio frequency technology such that signals detected by the electrodes 108 are passed to the apparatus 100 using radio frequency signaling.

Figure 3:
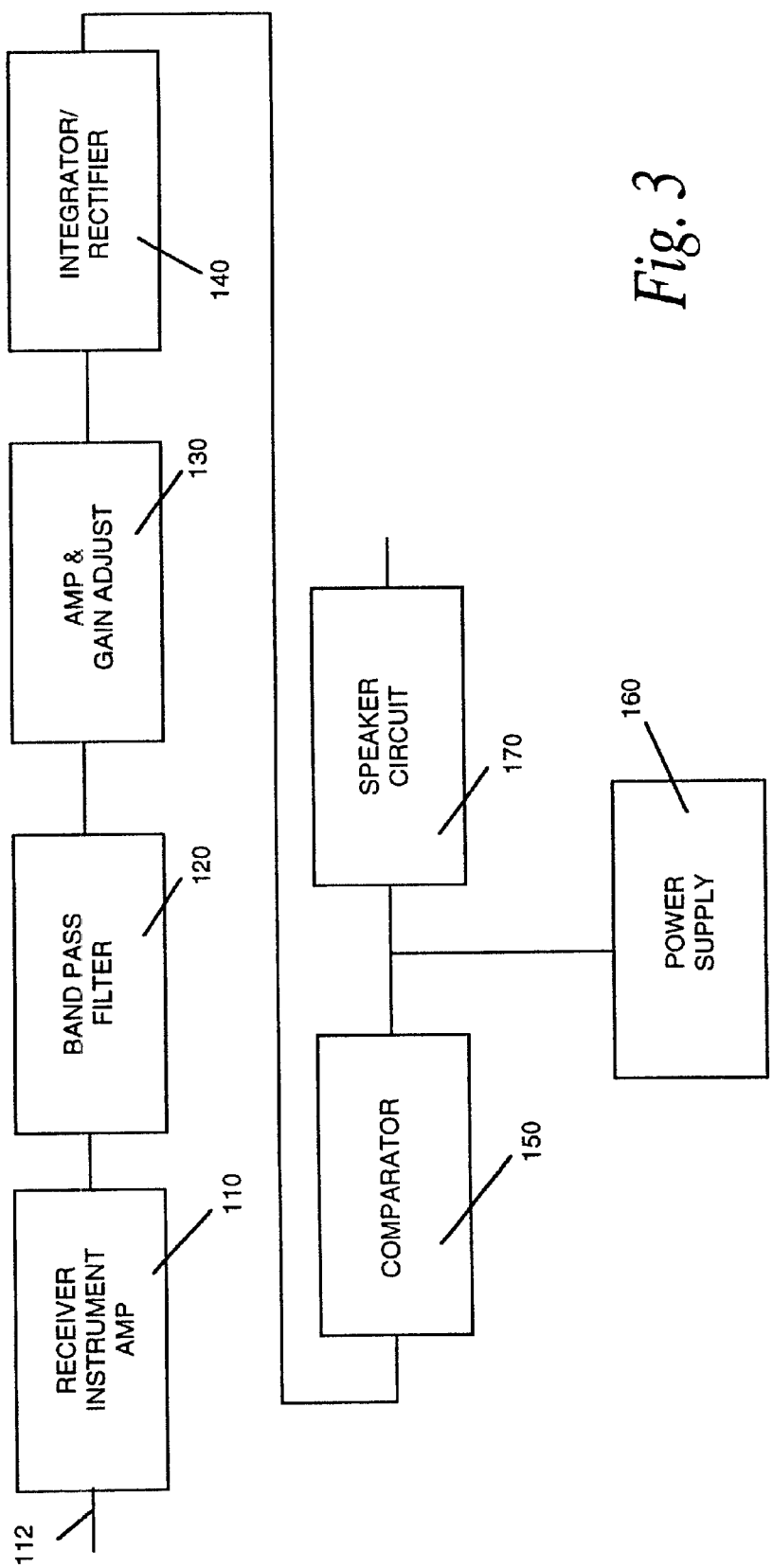

FIG. 3 is a block diagram of the electronic components of the apparatus 100. Signal line 112 provides a signal input from the wiring harness 102 (shown in FIG. 1a) to a receiver/instrument amplifier 110. The receiver/instrument amplifier 110 may be a differential amplifier that rejects common mode signals on the electrodes and passes differential signals, on the order of microvolts, that are generated as a result of neuron firings in the chosen muscle group. In an alternative embodiment, the receiver/instrument amplifier 110 may include a radio frequency receiver. The radio frequency receiver may receive outputs from the electrodes using a radio frequency communication path.

The output of the receiver/instrument amplifier 110 is fed to a band pass filter 120. The band pass filter 120 is designed to filter out high and low frequency signals and noise and to pass frequencies on the order of 100 Hz, for example.

The output of the band pass filter 120 passes to an amplifier and gain adjustment module 130. The amplifier and gain adjustment module 130 includes an adjustable gain setting that is operated using the switch 103 shown in FIG. 1a. Using the gain setting, the human subject is able to set a variable threshold for activation of a speaker in the apparatus 100. The amplifier and gain adjustment module 130 also provides amplification of the voltage signal from the electrodes.

The output of the amplifier and gain adjust module 130 is fed to an integrator/ rectifier 140. The integrator/rectifier 140 integrates the voltage signal when a certain voltage level is reached. The integrator/rectifier 140 also rectifies the voltage from AC to DC. The output of the integrator/rectifier 140 is passed to a comparator 150. The comparator 150 compares the integrated output of the integrator/rectifier 140 to a preset value, and when the preset value is exceeded, the integrator/regulator 140 causes an output signal to be generated at the comparator 150. The output signal from the comparator 150 is provided to a speaker circuit 170. The speaker circuit 170 includes a small speaker (not shown in FIG. 3) that provides a steady output signal when the threshold value set at the amplifier and gain adjust module 130 is exceeded. Finally, the apparatus 100 shown in FIG. 3 includes a power supply 160 that supplies power to the electronics. The power supply 160 may be a small DC power supply, such as a 9 volt battery, for example.

Figure 4:
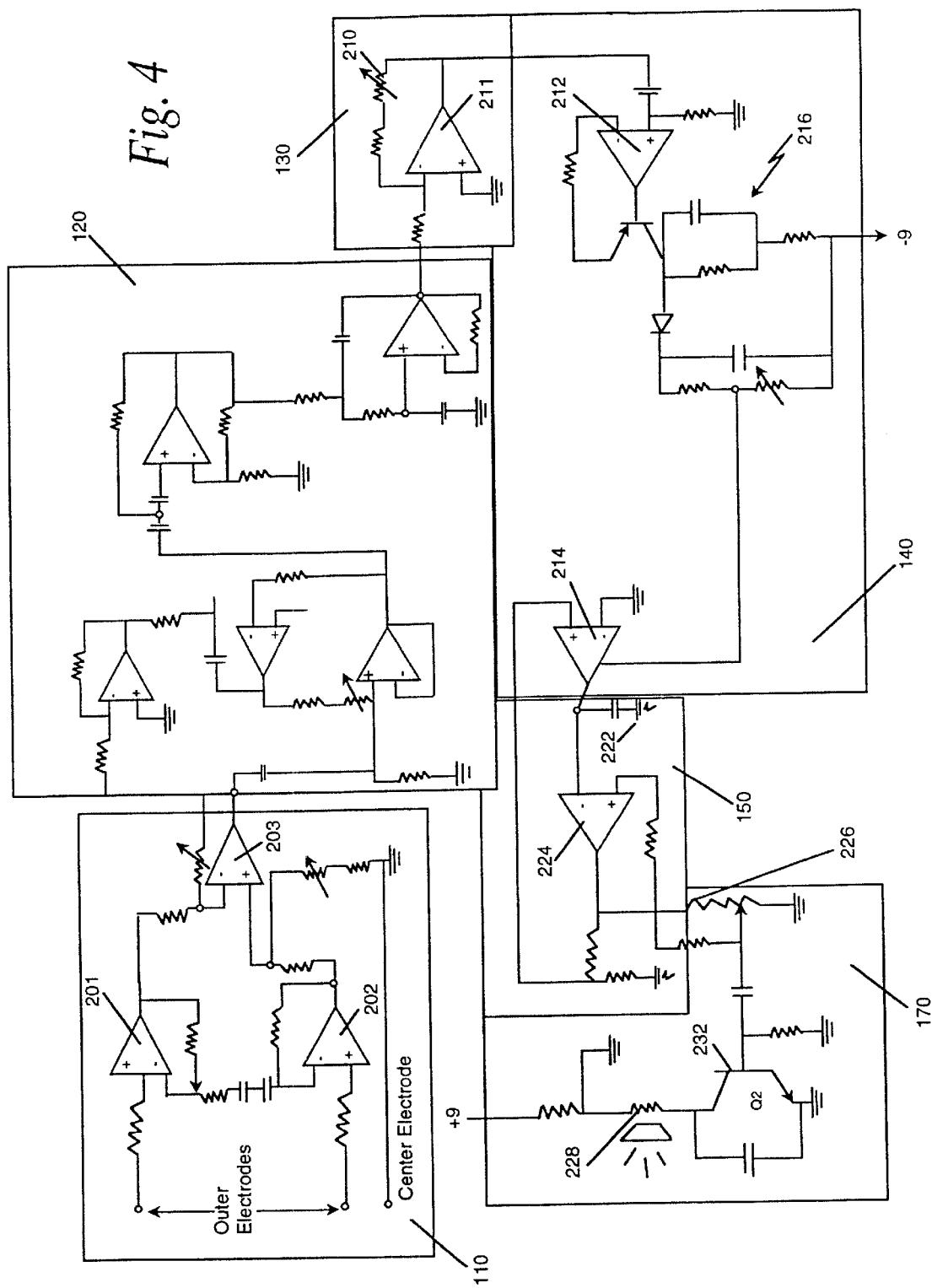

FIG. 4 is an electrical schematic showing the control and display circuitry of the apparatus of FIG. 1a. The electronics shown in FIG. 3 are grouped according to the block diagram components shown in FIG. 3. The electronics shown in FIG. 4 are well known devices that need not be explained in detail here. Various other arrangements and capacities of the electronics other than those shown in FIG. 4 may be used to produce a desired output. As shown in FIG. 4, outer electrode inputs are connected to the receiver/instrument amplifier 110, specifically to operational amplifiers 201 and 202. A center electrode input is shown grounded. A summing operational amplifier 203 measures the signal differences between the three electrode inputs.

The band pass filter 120 comprises a number of operational amplifiers that provide both high frequency and low frequency filtering. The schematic shown in FIG. 4 shows one arrangement of these operational amplifiers. The amplifier and gain adjust module 130 comprises an operational amplifier 211 and a gain adjust resister 210. The gain adjust resister 210 is operated by operation of the threshold switch 103 shown in FIG. 1a.

The integrator/rectifier 140 comprises operational amplifiers 212 and 214 and rectifier assembly 216. The rectifier assembly 216 converts AC voltage from the electrodes to DC voltage and the operational amplifiers 211 and 214 operate to integrate the output of the amplifier and gain adjust module 130 when the signal reaches a specified threshold value.

The comparator 150 includes an operational amplifier 224 and a charging capacitor 222. The capacitor 222 is charged by the output of the integrator/rectifier 140. The rate of charge of the capacitor 222 is determined by the integrated voltage out of the integrator/rectifier 140. The output of the operational amplifier 224 changes based on the state of the detected voltage, causing the capacitor 222 to discharge. The output of the capacitor 222 is fed to the speaker circuit 170. The speaker circuit 170 includes a speaker 228, a speaker volume control 226 and a transistor 232. The transistor 232 switches state to cause a clicking sound that is displayed by the speaker 228 at a rate determined by the measured voltage difference between the electrodes. The volume control 226 is used to adjust the volume displayed by the speaker 228.

Figure 5:
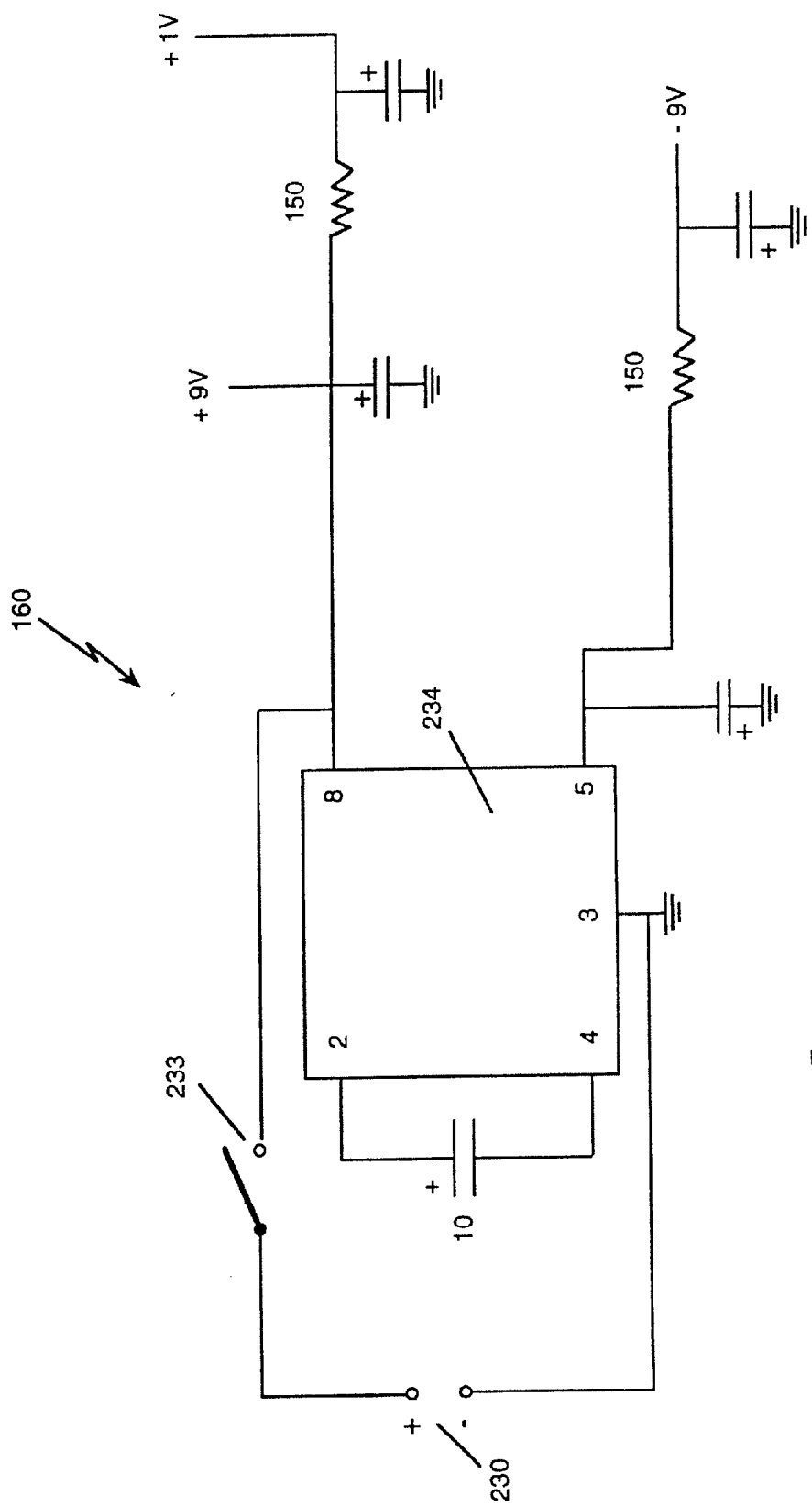

FIG. 5 is an electrical schematic of the power supply 160 shown in FIG. 3. The power supply 160 may include a nine volt battery 230, an on/off switch 233 and a negative voltage converter 234. The power supply 160 provides DC power at between 1 and 9 VDC to selected components in the apparatus 100.

In operation, the apparatus 100 of FIG. 3 produces a steady clicking sound, or similar audible feature indicating that a preset threshold value, indicative of a human subject's stress tolerance level has been exceeded. The apparatus 100 is placed is operation by first selecting a muscle group to which the electrodes are attached. The electrodes may be attached by any conventional attachment mechanism. Wires leading from the electrodes are coupled through wiring harness 102 shown in FIG. 1a to the instrument electronics. The apparatus 100 is turned on by placing the on/off switch 102 in the on position. The volume switch 102 is then operated to select a desired volume for output of the speaker 228. Finally, the human subject selects a threshold value by which operation of the apparatus 100 will occur by operating the switch 103 shown in FIG. 1a.

The apparatus 100 will then monitor voltage signals emanating from the muscle group selected by the human subject. When the differential voltage level reaches a certain value indicating that tension and stress have reached the threshold level, the apparatus 100, through the speaker plate 105, will display an audible signal. The human subject may then take actions to reduce the stress, while leaving the apparatus 100 connected and in operation. For example, the human subject may cease the activities that are causing the stress, such as typing, reading or other work related functions, or may relax certain parts of the body until the signal is reduced or stops.

By selecting an appropriate muscle group and an appropriate threshold setting, the human subject can learn to determine the onset of tension and stress and take actions to avoid the harmful effects by changing or moderating the behavior that leads to the stress. After repeatedly using the apparatus 100, the human subject can learn to become aware of the onset of stress without the use of the apparatus 100. The human subject may use the apparatus 100 continually for five work days, for example, to determine which work-related activities lead to a stress buildup. The human subject may learn that typing or keyboarding for more than two hours leads to stress buildup, as indicated by an output of the apparatus 100. The human subject could then limit typing or keyboarding sessions to less than two hours to avoid a stress condition. In the same manner, the human subject will be able to control other behavior that leads to stress so as to keep stress levels at the very minimum.

The apparatus 100 provides a convenient and portable mechanism for detecting stress and for providing an easily controllable signal that the human subject can interpret to indicate the onset of stress. The apparatus 100 can be easily adjusted to accommodate different individuals. In addition, the apparatus 100 is convenient to use in ambulatory settings, including in most work environments. The apparatus 100 has a low profile and may easily fit into a pocket of the human subject's clothing, may be attached by a velcro fastener, or may clip on, for example. The apparatus 100 comprises simple electronics that are inexpensive to produce and that can be operated without extensive training and skill.

What is claimed is:

1. An apparatus for detecting stress in a human subject, comprising:

an electronic circuit, wherein the electronic circuit includes a receiver for receiving signals indicative of stress in the human subject, a band pass filter for filtering noise from the received signals, a gain adjustment module including an operational amplifier and a gain adjust resistor for adjusting a threshold stress value, an integrating and rectifying module for integrating a voltage signal and rectifying the voltage from AC to DC, the integrating and rectifying module having one or more operational amplifiers and a rectifier assembly, a comparator having an operational amplifier and a charging capacitor for comparing the integrated voltage signal to a preset voltage value, and a power supply;

an output device that provides a signal indicative of the stress, wherein the signal is proportional to the stress; and a compact housing that contains the electronic circuit and the output device.

2. The apparatus of claim 1, further comprising electrode leads, each of the electrode leads coupled to a corresponding electrode, wherein the electrode leads carry a voltage signal from a selected muscle group, the voltage signal comprising the indication of stress in the human subject.

3. The apparatus of claim 1, further comprising a speaker module, wherein the signal is an audible signal and wherein the audible signal is displayed by the speaker module.

4. The apparatus of claim 3, wherein the speaker module comprises a volume control adjustable to determine an intensity of the audible signal.

5. The apparatus of claim 1, wherein the housing is sized to fit into a shirt pocket.

6. The apparatus of claim 1, wherein the electronic circuit is provided on a printed circuit board.

7. The apparatus of claim 1, wherein the compact housing is concealable during operation.

8. The apparatus of claim 1 further comprising wireless electrodes for transmitting a radio frequency signal indicating the stress in the human subject.

9. A system for detecting stress in a human subject, comprising:

one or more wireless electrodes, wherein the one or more wireless electrodes are incorporated into a garment;

an electronic circuit that measures the output of the one or more wireless electrodes and provides an indication of stress, the electronic circuit comprising;

a radio frequency receiver for receiving outputs from the one or more wireless electrodes, using a radio frequency communication path;

a threshold mechanism adjustable to pre-set a stress point; and an output circuit that provides an output indicative of stress in the human subject.

10. The system of claim 9, wherein the threshold mechanism is adjustable by the human subject, based on an expectation of stress by the human subject.

11. The system of claim 9, wherein the output circuit is a speaker circuit, wherein the speaker circuit provides an audible indication when the voltage difference signal reaches the adjustable pre-stress set point.

12. The system of claim 9, wherein the one or more electrodes comprise three electrodes.

13. The system of claim 8, further comprising a compact housing, wherein the electronic circuit is contained within the compact housing.

14. The system of claim 13, wherein the compact housing is concealable during operation.

15. The system of claim 14, further comprising means to attach the apparatus to the human subject, wherein the compact housing is sized to fit into a shirt pocket.

16. The system of claim 9, wherein the garment is an undershirt.

17. The system of claim 9, wherein the garment is a band.

18. The system of claim 17, wherein the band is configured to fit across the chest of the human subject.

19. The system of claim 17, wherein the band is configured to fit across the forehead of the human subject.

20. A method for detecting and reducing stress in a human subject comprising attaching one or more wireless electrodes to a selected muscle group, wherein the one or more wireless electrodes are incorporated into a garment;

receiving a pre-set threshold selection indicative of an onset of a stress condition;

measuring a differential signal from the one or more wireless electrodes;

comparing the differential signal to the pre-set threshold; and providing an output signal when the pre-set threshold is exceeded.

21. The method of claim 20, wherein the output signal is an audible signal.

22. The method of claim 21, further comprising providing the audible signal at a rate indicative of an amount by which the pre-set threshold is exceeded.

23. The method of claim 22, further comprising providing the audible signal until the measured differential signal is less than the pre-set threshold.

24. The method of claim 20, wherein the differential signal is compared to the pre-set threshold in an electronic circuit housed in a compact housing.

25. The method of claim 20, further comprising:

using the method repeatedly such that the human subject learns factors that indicate the onset of the stress condition; and modifying the factors to reduce the stress.

26. The method of claim 20, wherein the electronic circuit is housed in a compact housing concealable during operation.

27. The method of claim 20, wherein the garment is an undershirt.

28. The method of claim 20, wherein the garment is a band.

29. The method of claim 27, wherein the band is configured to fit across the human subject's chest.

30. An electronic circuit that indicates stress in a human subject, wherein the electronic circuit comprises:

a receiver for receiving signals indicative of stress in the human subject;

a band pass filter for filtering noise from the received signals;

a gain adjustment module for adjusting a threshold stress value, the gain adjustment module having an operational amplifier and a gain adjust resistor;

an integrating and rectifying module for integrating a voltage signal and rectifying the voltage from AC to DC, the integrating and rectifying module having one or more operational amplifiers and a rectifier assembly;

a comparator for comparing the integrated voltage signal, from the integrating and rectifying module, to a preset voltage value, the comparator having an operational amplifier and a charging capacitor; and a power supply.

31. The electronic circuit of claim 30, wherein the receiver is a radio frequency receiver, for receiving radio frequency signals from one or more wireless electrodes.

32. The electronic circuit of claim 30, wherein the receiver is a differential amplifier that provides a voltage difference signal based on a differential voltage detected by one or more electrodes, wherein the one or more electrodes are connected to the receiver by leads.

* * * * *

UNITED STATES PATENT AND TRADEMARK OFFICE
CERTIFICATE OF CORRECTION

PATENT NO.   : 6,493,578 B1
DATED        : December 10, 2002
INVENTOR(S)  : Michael DeFeo It is certified that error appears in the above-identified patent and that said Letters Patent is hereby corrected as shown below:

Column 7,
Lines 49-50, please correct claim 13 to read as follows:
13.     The system of claim 9, further comprising a compact housing, wherein the electronic circuit is contained within the compact housing.

Signed and Sealed this

Twenty-seventh Day of May, 2003

JAMES E. ROGAN
*Director of the United States Patent and Trademark Office*